United States Patent [19]

Shiber

[11] Patent Number: 5,024,651
[45] Date of Patent: * Jun. 18, 1991

[54] ATHERECTOMY SYSTEM WITH A SLEEVE

[75] Inventor: Samuel Shiber, Woburn, Mass.

[73] Assignee: Surgical Systems & Instruments, Inc., Mundelein, Ill.

[ * ] Notice: The portion of the term of this patent subsequent to Jan. 16, 2007 has been disclaimed.

[21] Appl. No.: 322,497

[22] Filed: Mar. 13, 1989

Related U.S. Application Data

[63] Continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, and a continuation-in-part of Ser. No. 205,479, Jun. 13, 1988, Pat. No. 4,883,458, and a continuation-in-part of Ser. No. 225,880, Jul. 29, 1988, Pat. No. 4,842,579, said Ser. No. 78,042, Ser. No. 205,479, and Ser. No. 225,880, each is a continuation-in-part of Ser. No. 874,546, Jun. 16, 1986, Pat. No. 4,732,154, which is a continuation-in-part of Ser. No. 609,846, May 14, 1984, abandoned.

[30] Foreign Application Priority Data

| Jun. 15, 1987 | [EP] | European Pat. Off. | 87305277.3 |
| Jun. 16, 1987 | [CA] | Canada | 539735 |
| Jun. 16, 1987 | [JP] | Japan | 62-150056 |
| Sep. 15, 1988 | [CA] | Canada | 577462 |
| Sep. 16, 1988 | [EP] | European Pat. Off. | 88308555.7 |
| Sep. 30, 1988 | [JP] | Japan | 63-247261 |

[51] Int. Cl.$^5$ ............................................. A61B 17/32
[52] U.S. Cl. ........................................ 604/22; 606/159
[58] Field of Search ................ 606/159, 170, 180; 604/22, 95, 264, 267

[56] References Cited

U.S. PATENT DOCUMENTS

| 4,207,874 | 6/1980 | Choy | 604/7 X |
| 4,669,469 | 6/1987 | Gifford III et al. | 606/159 |
| 4,772,258 | 9/1988 | Marangoni et al. | 606/159 X |
| 4,790,812 | 12/1988 | Hawkins Jr. et al. | 606/159 X |
| 4,894,051 | 1/1990 | Shiber | 604/22 |

Primary Examiner—Robert A. Hafer
Assistant Examiner—Kerry Owens
Attorney, Agent, or Firm—Samuel Shiber

[57] ABSTRACT

An atherectomy system for removing an obstruction from within a patient's vessel, comprising a flexible guide-wire insertable into the vessel, a flexible rotary catheter for coring and ingesting obstruction material, insertable into the vessel over the flexible guide-wire, the flexible rotary catheter having coring means at its distal end and coupling means for connecting it to a power source, at its proximal end, a sleeve in which the flexible rotary catheter is slidably disposed, the sleeve having a window near its open distal end.

14 Claims, 2 Drawing Sheets

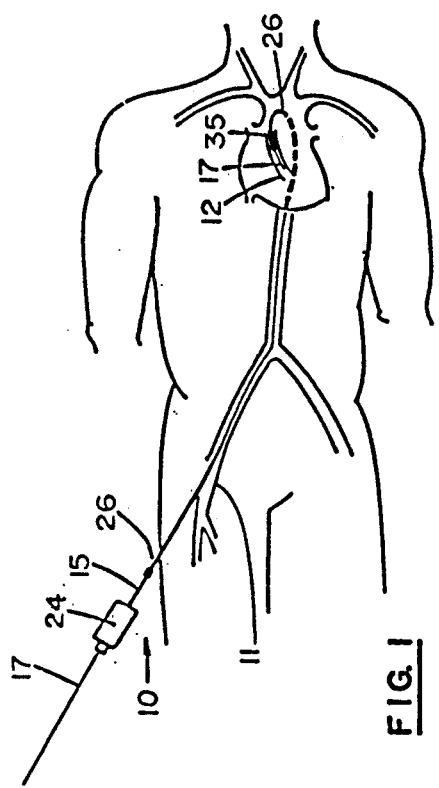
FIG. 1
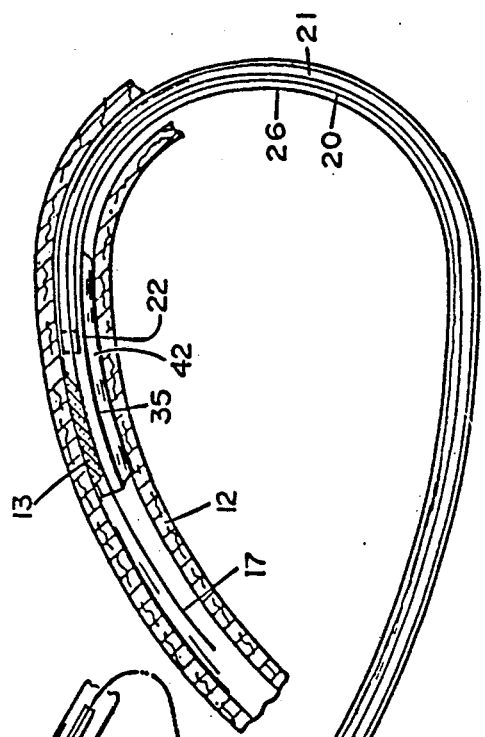
FIG. 2
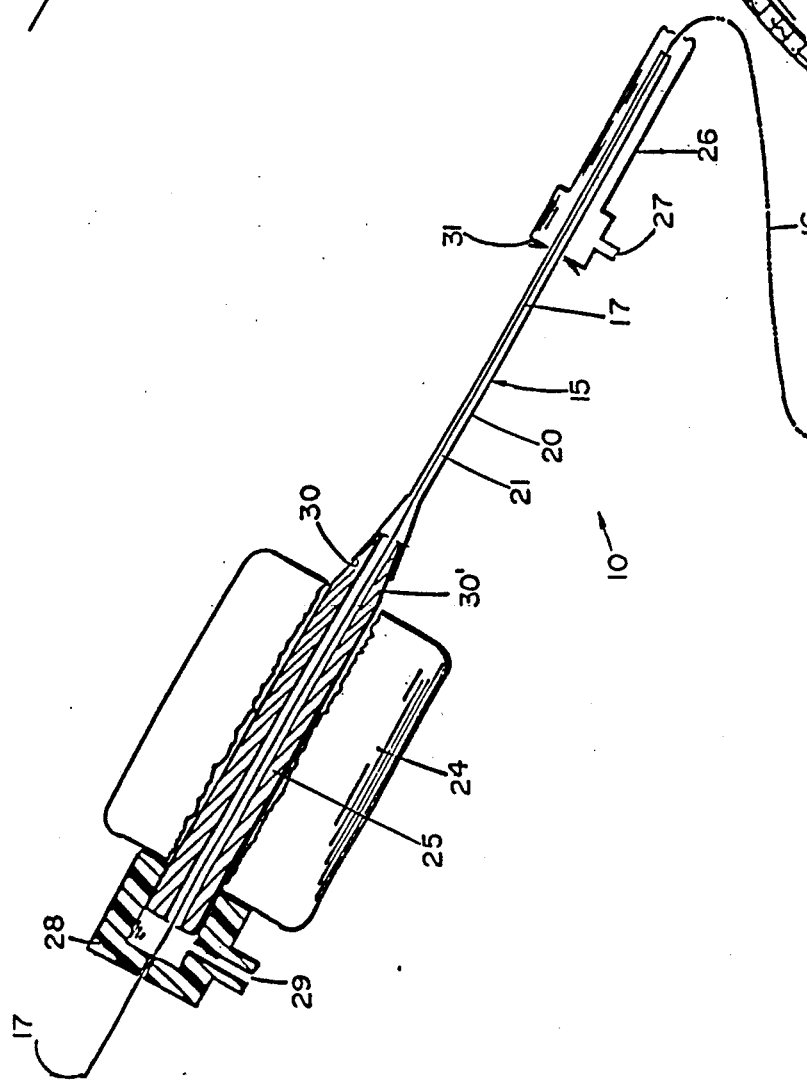

ATHERECTOMY SYSTEM WITH A SLEEVE

CROSS REFERENCE TO OTHER APPLICATIONS

This application is a continuation in part (CIP) of application Ser. No. 07/286,509 Dec. 19, 1988 which is a CIP of application Ser. No. 07/243,900 filed Sep. 13, 1988 which is a CIP of three applications, application Ser. No. 07/078,042 filed Jul. 27, 1987, application Ser. No. 07/205,479 filed Jun. 13, 1988 and application Ser. No. 07/225,880 filed Jul. 29, 1988. These three applications are CIPs of application Ser. No. 07/018,083 filed Feb. 24, 1987, which is a CIP of application Ser. No. 06/874,546 filed Jun. 16, 1986 (now U.S. Pat. No. 4,732,154) which is a CIP of application Ser. No. 06/609,846 filed May 14, 1984 (abandoned).

All the above applications are being incorporated herein by reference.

BACKGROUND OF THE INVENTION

With age a large percentage of the population develops atherosclerotic arterial obstructions resulting in a diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Some of the problems with angioplasty are that it injures the arterial wall, it creates a rough lumen and in substantial number of the cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy catheter which is insertable and advancable in an artery over a flexible guide-wire. The flexible rotary catheter is equipped with a coring means at its distal end to core and extract obstruction material and create a smooth lumen without cracking the arterial wall.

The catheter is slidable in a sleeve having a window near its distal open end. Obstruction material can enter the sleeve through the window and the open distal end, to be cored and ingested by the flexible rotary catheter.

The sleeve is slidable over the catheter, or over a standard dilator, for insertion thereof into an artery and further into an obstruction. This facilitates treatment of eccentric lesions and the cleaning of larger arteries through a smaller puncture at the point of insertion oi the system into the vessel.

These and other objectives of the invention will become apparent from the following discussion and the accompanying drawings.

BRIEF DESCRIPTION OF THE FIGURES

FIG. 1 schematically shows a general view of an atherectomy system inserted at the groin area, through a patient's arterial system, into his obstructed coronary artery.

FIG. 2 shows a cross sectioned view of the atherectomy system. The middle portion of the system is represented with a phantom line, due to space limitations on the drawing sheet.

FIG. 5' shows a cross sectional view along line 5—5 marked on FIG. 4 of the window region of a sleeve of the embodiment, on an enlarged scale, showing the reinforcing rib.

DETAILED DESCRIPTION OF THE DRAWINGS

Figure 5:
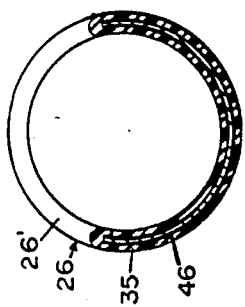
FIG. 5 shows a cross sectional view along line 5—5 marked on FIG. 4 of the embodiment, in an artery, prior to pressurizing the inflatable chamber.
Figure 5:
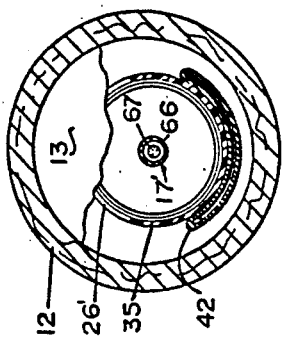
Figure 7:
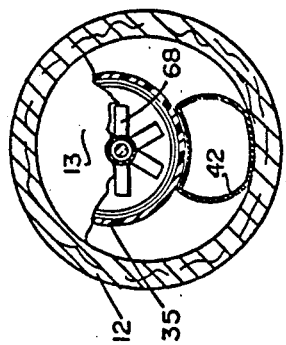
FIG. 7 shows a cross sectional view along line 7—7 marked on FIG. 6 of the embodiment, in an artery, with the inflatable chamber pressurized and with the distal barrier means expanded.
Figure 3:
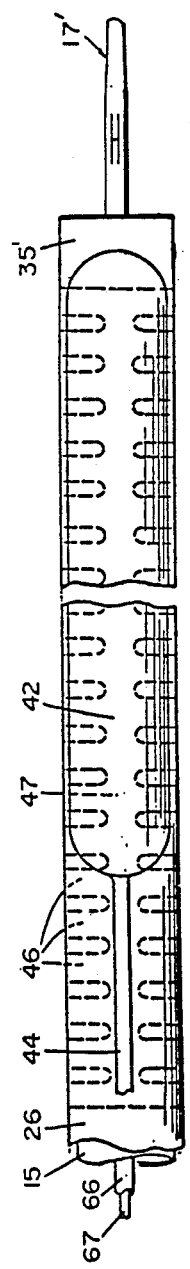
FIG. 3 shows a bottom view of a distal portion of an embodiment of the system.

FIG. 1 schematically shows a general view of an atherectomy system with a sleeve, 10, introduced percutaneously (through the skin) into a patient's artery 11, at the groin area. The system's distal end is inserted through the arterial system to reach a work site in a coronary artery 12 while its proximal end remains outside the patient's body As shown in FIG. 2 the atherectomy system comprises several elongated parts in a nested relationship, and their ends shall be referred to as "distal" meaning the end which goes into the vessel and "proximal" meaning the other end, thus, "distal direction" or "distally" shall indicate a general direction from the proximal end to the distal end, and "proximal direction" or "proximally" shall refer to an opposite direction.

As further shown in FIG. 2, the distal portion of the system 10 is placed in the diseased coronary artery 12 (same numbers are used to indicate similar items throughout the FIGURES) containing an eccentric atherosclerotic obstruction 13. The system's mid portion is represented by a phantom line 16 because of space limitation of the drawing sheet.

The system comprises:

A flexible guide-wire 17 insertable through the human vascular system.

A flexible rotary-catheter 15, rotatable and slidable over the guide-wire, having a wall 20 defining a longitudinal channel 21. Coring means in the form of a tubular blade 22 is mounted at the distal end of the flexible rotary-catheter. The tubular-blade defines a through-hole which forms with the channel 21 a continuous passage for accepting the obstruction material ingested into the through-hole. A variety of rotary coring means have been shown in my incorporated by reference applications: Tubular blades, single tooth blades, blades which are essentially the distal end of the flexible rotary catheter and radiation emitting devices. Some of these rotary coring means are incorporated into, or are part of, the distal end of the flexible rotary catheter and have no internal wall of their own, in which case the continuous passage consists of the channel 21.

Frictional losses which develop between the flexible rotary-catheter and a sleeve 26 strain the flexible rotary-catheter and the motor. These frictional losses are more pronounced with an obese patient where the system is introduced into the femoral artery at the groin, and has to assume a sharp bend at the point of entry due to patient's protruding abdomen. To reduce these frictional losses the diameter of the proximal portion of the flexible rotary-catheter is decreased at a point marked 15' on FIG. 2. Such a diametrical decrease does not interfere with the ingestion of obstruction material as long as a sufficient distal portion of a full diameter flexible rotary-catheter is left to accept the material. For example, a flexible rotary-catheter for removing an obstruction from peripheral arteries having a total length of 50 centimeters (cm) can be manufactured with a 35 cm proximal portion of 2.5 millimeters (mm) diameter and a 15 cm distal portion of 3 mm diameter. However, if the obstruction is long the location of the diametrical transition point 15' can be moved proximally to increase the catheter's material ingestion capacity.

A motor 24 has a hollow shaft 25 with a tapered distal end 30' which engages a coupling means in the form of a matching tapered seat 30 formed at the proximal end of the flexible rotary-catheter.

The sleeve 26 has a window region 35 with a biasing means near its open distal end. The sleeve defines in the vessel a trajectory for the coring means to move along and it can also serve as an introducer of the system into the artery. Alternatively, the sleeve can be introduced through a separate introducing sheath. The sleeve has a port 27 through which it accepts contrast or irrigating, lubricating and/or radio opaque contrast fluids and delivers them through its distal end to the work site. A seal 31 prevents the fluid from escaping through the sleeve's proximal end.

A rotary joint 28 has a port 29 which is connected through the hollow shaft 25 to the continuous passage and can be used for introducing a negative pressure in the continuous passage to assist in sucking and drawing the cored obstruction material into it. The suction and a mechanical action resulting from the relative motion between the rotating inner wall of the continuous passage and the flexible guide-wire effectively ingests the cored material into the continuous passage for subsequent removal thereof out of the patient's body. In an early stage of the procedure, prior to ingesting obstruction material, the fluid route connecting the port 29 and the distal end of the flexible rotary-catheter can be used as an alternative route for delivering fluids to the work site. The flexible guide-wire slidably passes through a close fitting hole formed at the proximal end of the rotary joint.

FIGS. 3 to 7 show the distal end of the embodiment of an atherectomy system with a sleeve for removing an obstruction from within the patient's vessel, artery 12, comprising:

a flexible guide-wire 17', the flexible rotary-catheter 15 with coring means in the form of the tubular-blade 22 at its distal end, for coring and ingesting obstruction material, insertable into the vessel over the flexible guide-wire.

The sleeve 26 in which the flexible rotary-catheter is rotatably and slidably disposed and which in turn is slidable over the flexible rotary catheter, has an open proximal end, an open distal end 35' and a window 26' located near the distal end. The window is intended to be placed in the arterial lumen so that the obstruction material is urged to enter it through the window and then the material is cored and ingested by the advancing flexible rotary catheter along the phantom line which is marked on FIG. 6.

The window region has cross section in the shape of an incomplete circle, shown in FIGS. 5, 5' and 7, which positively contains the flexible rotary-catheter by surrounding more than half of its periphery. The window region's cross section is stabilized by reinforcing means in the form of semicircular ribs like elements 46 (note FIG. 5'). The elements 46 are tied together by a spine like element 47 which substantially contributes to the strength and the torque transmission ability of the window region while allowing it to bend. Therefore, elements 46 and 47, which can be made from flat stainless steel sheet material, stabilize the cross section of the window region to maintain a proper relationship between the window region's cross section and the tubular-blade but they allow the window region to bend and conform to the arterial curvature and they enable the user to rotate the window in the artery to position it toward the obstruction material.

The window region has a selectively actuable biasing means in the form of an inflatable chamber 42 for biasing the window towards the obstruction material so that the material is urged to enter the sleeve through the window, preparatory to the flexible rotary catheter advancing distally and rotating in the sleeve, over the window, coring and ingesting this material. Then the window can be rotated a part of a turn, the flexible rotary catheter can be proximally retracted in the sleeve past the window, which is then re-biased toward the remaining obstruction material and additional pass or passes can be made as needed. Thus, eccentric obstructions and large diameter arteries can be de-bulked and re-canalizing through a smaller puncture wound in the vessel's wall.

Figure 4:
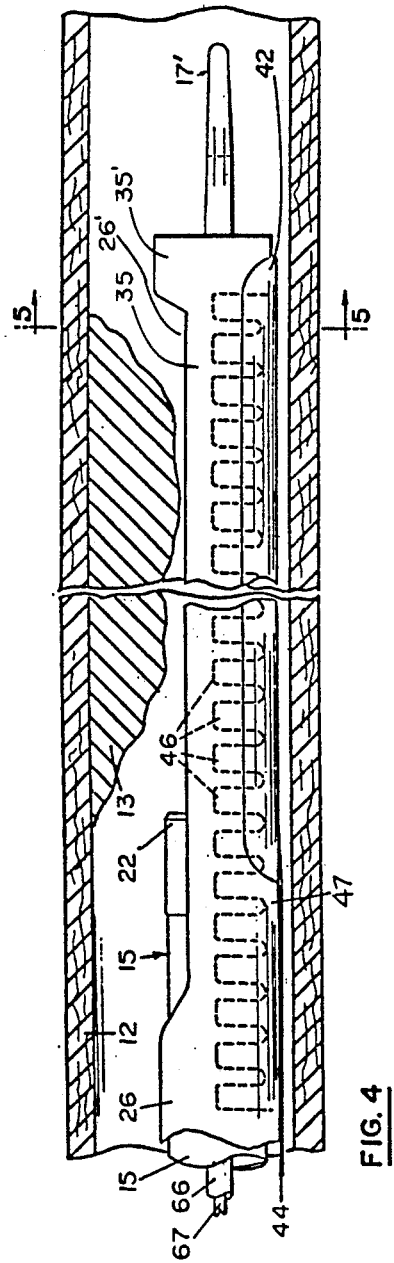
FIG. 4 shows a side view of a distal portion of the embodiment, in an artery, prior to pressurizing an inflatable chamber and prior to expanding a barrier means at the distal end of the flexible guide-wire.
Figure 6:
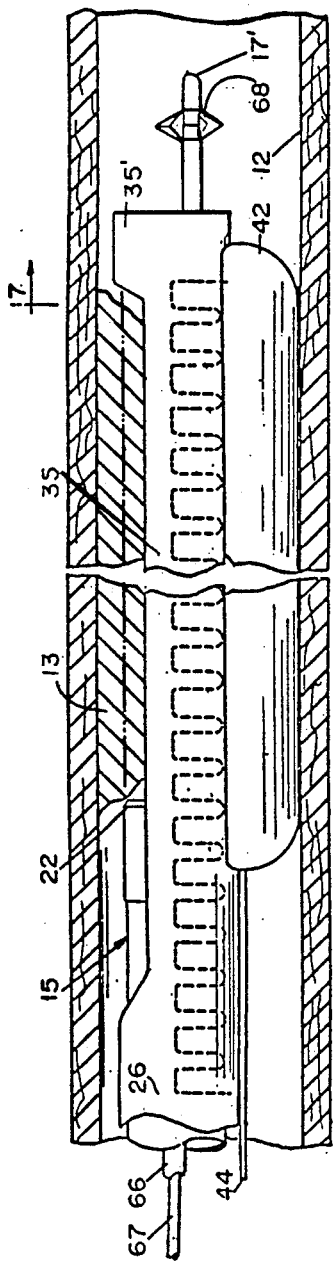
FIG. 6 shows a side view of a distal portion of the embodiment, in an artery, with the inflatable chamber pressurized through the inflatable tube Obstruction material is accepted into a sleeve through a window in order to be cored and removed along a phantom line. The distal barrier means are expanded.

An inflatable tube 44, for inflating the chamber 42, is formed integral with the chamber. When the chamber is inflated the tube is also slightly inflated, as shown in FIG. 6, however, prior to inflation the tube remains flat and negative pressure can be applied to the tube to further flatten it, as shown in FIG. 4, minimizing the tube's contribution to the size of the puncture wound that will be needed to introduce the sleeve into the patient's body. Alternatively, the inflation tube can be defined in the wall of the sleeve particularly if the sleeve is an extrusion, in which case the tube can be co-extruded with the main lumen of the sleeve. The inflation lumen is connected at its distal end to the chamber and at its proximal end it is connectable to inflation means such as a syringe.

The flexible guide-wire 17' has a distal barrier means in the form of a thin jacket 66 over a core wIre 67 The jacket and core wIre are bonded at their distal tip, and by pulling the core wire and sliding it proximally relative to the jacket the arms 68, which are formed by multiple slits in the sleeve, are extended radially. Barrier means as well as additional suitable flexible guide-wire designs are discussed in my above incorporated patent applications.

OPERATION

A process for removing an obstruction from a vessel comprises the following steps:

Inserting into a vessel and into an obstruction in the vessel a flexible guide-wire.

Inserting into the vessel, over the flexible guide wire a dilator.

Inserting into the vessel over the dilator an introducer.

Withdrawing the dilator out of the introducer. As previously explained, the sleeve can also be the introducer, alternatively, the sleeve can be inserted into the vessel through the introducer.

Distally advancing over the flexible guide-wire a flexible rotary catheter through the obstruction, either by coring a passage through the obstruction or, if the original lumen of the obstruction is large enough, by simply passing the catheter through it.

Inserting an open distal end of a sleeve and a window into the obstruction. The insertion oi the sleeve can be done over the flexible rotary catheter, using it as a guide for safely advancing the sleeve. The clearance between the sleeve's opening at its distal end to the flexible rotary catheter is small, therefore, when the sleeve is advanced over the flexible rotary catheter the probability of its taking a big bite of arterial wall is minimized.

Retracting the rotary coring means past the window, biasing the window against the obstruction material to cause the later to enter the sleeve through the window and then advancing and rotating the flexible rotary catheter, coring and ingesting the obstruction material that has entered the sleeve.

If the lumen through the obstruction is to be further increased by removal of additional obstruction material the above step can be repeated as needed, and prior to such repetitions the window can be rotated and moved along the artery so that it faces different areas of the obstruction.

The amount of biasing can be regulated by the inflation pressure of a chamber attached to the bottom of the window region.

Negative pressure applied to the proximal end of the continuous passage can be used to cooperate with a mechanical action in enabling the cored obstruction material into the continuous passage.

It should be noted that the atherectomy system can be manufactured in different diameters and lengths depending on the size and site of artery that it is intended for and on whether the system is to be used percutaneously (that is through the skin) or intra-operatively (that is when the vessel is surgically exposed for inserting the system into the vessel). It can also be noted from the present application and the incorporated applications that components of the atherectomy system can be made in several ways: The flexible rotary catheter can be made from plastic or metal and either version can be equipped with an internal helical step. The coring means can be a tubular-blade, a heated tubular blade or a radiation emitting means such as an optical fiber located at a wall of the flexible rotary catheter carrying laser energy, or other means which core and ingest an obstruction disposed in front of it. By combining a sleeve having a certain biasing means, a certain flexible rotary catheter and a certain flexible guide-wire a variety of species can be made to match the system's characteristics with the specific disease characteristics of an individual patient. Similarly, various of the steps described above can be altered, deleted or additional steps can be added to suite an individual case.

This is helpful, since the clinical characteristics of arterial atherosclerotic obstructions vary in geometry, hardness, and accessibility from one patient to another. It should be further understood that various modifications and substitutions may be made without departing from the spirit of the invention or the scope of the claims.

I claim:

1. An atherectomy system for removing an obstruction from within a patient's vessel, comprising in combination:
    a flexible guide-wire insertable into the vessel,
    a flexible rotary catheter for cutting and ingesting obstruction material, insertable into the vessel over said flexible guide-wire, said flexible rotary catheter having a blade at its distal end and coupling means for connecting it to a power source, at its proximal end,
    a sleeve, in which said flexible rotary catheter is slidably and rotatably disposed, having a window near its open distal end.

2. An atherectomy system of claim 1, said sleeve has, at a region of said window, a cross section which positively contains said flexible rotary catheter.

3. An atherectomy system as in claim 1, said sleeve having a selectively actuable biasing means for biasing said window against said obstruction.

4. An atherectomy system as in claim 3, said biasing means comprise an inflatable chamber attached to a bottom side of said window region.

5. An atherectomy system as in claim 1, wherein suction is applied at a proximal end of said flexible rotary catheter to pull the cut obstruction material proximally in said flexible rotary catheter.

6. An atherectomy system as in claim 1, said blade being a tubular-blade.

7. An atherectomy system as in claim 1, said blade being a radiation emitting device.

8. An atherectomy system as in claim 1, said flexible rotary-catheter having a decreased diameter in its proximal section to reduce frictional losses between said flexible rotary-catheter and said sleeve at the area of entering the patient's body.

9. An atherectomy system as in claim 1, said flexible guide-wire having a radially extending distal barrier means to counter distal movement of obstruction material.

10. An atherectomy system as in claim 9, wherein said distal barrier means can elasticly contract to pass through a narrowed lumen.

11. An atherectomy system as in claim 9, wherein said distal barrier means are selectively expandable.

12. An atherectomy system as in claim 1, wherein means for introducing fluids into the vessel are connected to said sleeve.

13. A process for removing an obstruction from a vessel, comprising the following steps:
    inserting into a vessel and through an obstruction therein, a flexible guide wire,
    distally advancing over the flexible guide-wire and through the obstruction a flexible catheter,
    distally advancing, over the flexible catheter, a sleeve having a window near its open distal end and placing the window in the obstruction,
    biassing the window against the obstruction urging obstruction material to enter the sleeve through the window,
    proximally retracting the flexible catheter into the sleeve past the window,
    distally advancing the flexible catheter in said sleeve past the window, cutting and ingesting the obstruction material that has entered the sleeve through said window.

14. A process as in claim 13, wherein suction is used to enable the cut obstruction material proximally into the flexible catheter.

* * * * *